US011006843B1

(12) United States Patent
Badee et al.

(10) Patent No.: US 11,006,843 B1
(45) Date of Patent: May 18, 2021

(54) SYSTEM AND METHOD OF DETERMINING BREATHING RATES FROM OSCILLOMETRIC DATA

(71) Applicant: Cloud DX, Inc., Brooklyn, NY (US)

(72) Inventors: Vesal Badee, Kitchener (CA); Sara Ross-Howe, Campbellville (CA); Josh Haid, Kitchener (CA); Lamiaa Amzil, Waterloo (CA); Cezar Morun, Kitchener (CA); Bonghun Shin, Waterloo (CA)

(73) Assignee: CLOUD DX, INC., Brooklyn, NY (US)

( * ) Notice: Subject to any disclaimer, the term of this patent is extended or adjusted under 35 U.S.C. 154(b) by 0 days.

(21) Appl. No.: 16/998,361

(22) Filed: Aug. 20, 2020

(51) Int. Cl.
    *A61B 5/022* (2006.01)
    *A61B 5/021* (2006.01)
    *A61B 5/00* (2006.01)
    *A61B 5/08* (2006.01)

(52) U.S. Cl.
    CPC ...... *A61B 5/02225* (2013.01); *A61B 5/02116* (2013.01); *A61B 5/02125* (2013.01); *A61B 5/02141* (2013.01); *A61B 5/08* (2013.01); *A61B 5/6824* (2013.01); *A61B 5/7207* (2013.01); *A61B 5/742* (2013.01); *A61B 2562/0219* (2013.01)

(58) Field of Classification Search
    None
    See application file for complete search history.

(56) References Cited

U.S. PATENT DOCUMENTS

| | | | |
|---|---|---|---|
| 5,094,244 | A | 3/1992 | Callahan et al. |
| 5,682,898 | A | 11/1997 | Aung et al. |
| 10,022,053 | B2 | 7/2018 | Li et al. |
| 10,349,849 | B2 | 7/2019 | Knoll |
| 2003/0163054 | A1 | 8/2003 | Dekker |

(Continued)

OTHER PUBLICATIONS

Di Marco, Luigi Yuri, et al., Effects of Deep Breathing on Blood Pressure Measurement in Healthy Subjects, Computing in Cardiology 2012, vol. 39, pp. 745-748 (Year: 2012).*

(Continued)

*Primary Examiner* — Etsub D Berhanu
*Assistant Examiner* — Aurelie H Tu
(74) *Attorney, Agent, or Firm* — Stephen E. Zweig

(57) ABSTRACT

A system and method for determining the breathing rate of a patient using only an oscillometric device as the physiological sensor. Here, the oscillometric device is mounted on a patient's limb, and oscillometric pulse waveforms are obtained as the device's cuff deflates, thus obtaining pulse wave signals and artifact signals over multiple patient breaths. A computer processor analyzes these signals, and removes artifacts according to various algorithms. The resulting signal can be viewed as containing both an amplitude modulated envelope of pulse waves (AM signals) and a frequency modulated sequence of pulses at various time intervals (FM signals). The main harmonics of the AM and FM signals both contain breathing rate data, and system accuracy can be improved by comparing the AM harmonics with the FM harmonics. The final breathing rate data, often a function of the AM and FM harmonics, is output or stored in memory.

18 Claims, 18 Drawing Sheets

(56) References Cited

U.S. PATENT DOCUMENTS

| | | | | |
|---|---|---|---|---|
| 2008/0167541 | A1* | 7/2008 | Takala | A61B 5/7207 |
| | | | | 600/323 |
| 2009/0278728 | A1* | 11/2009 | Morgan | A61B 5/113 |
| | | | | 342/115 |
| 2011/0054330 | A1* | 3/2011 | Pfeiffer | A61B 5/02233 |
| | | | | 600/490 |
| 2012/0302900 | A1* | 11/2012 | Yin | A61B 5/0816 |
| | | | | 600/484 |
| 2016/0183846 | A1* | 6/2016 | Derkx | A61B 5/7264 |
| | | | | 600/534 |
| 2016/0324488 | A1* | 11/2016 | Olsen | A61B 5/14552 |
| 2017/0156606 | A1* | 6/2017 | Ferber | A61B 5/14539 |
| 2017/0164850 | A1* | 6/2017 | Murphy | A61B 5/7275 |
| 2017/0273582 | A1 | 9/2017 | Kawamoto et al. | |
| 2018/0146926 | A1* | 5/2018 | Ishikawa | A61B 5/02416 |

OTHER PUBLICATIONS

Chen and Chen, "A method for extracting respiratory frequency during blood pressure measurement, from oscillometric cuff pressure pulses and Korotkoff sounds recorded during the measurement" 2016 38th Annual International Conference of the IEEE Engineering in Medicine and Biology Society (EMBC).

Gui et. al., "Pulse interval modulation-based method to extract the respiratory rate from oscillometric cuff pressure waveform during blood pressure measurement" Computing in Cardiology (CinC) Sep. 2017—ieeexplore.ieee.org.

Cannesson et. al., "Does the Pleth Variability Index Indicate the Respiratory Induced Variation in the Plethysmogram and Arterial Pressure Waveforms?" Anesthesia & Analgesia 106 (4) Apr. 2008, pp. 1189-1194.

* cited by examiner

Time (arbitrary units) ⟶

Fig. 9

Time (arbitrary units) →

Time (arbitrary units) →

Time (arbitrary units) →

SYSTEM AND METHOD OF DETERMINING BREATHING RATES FROM OSCILLOMETRIC DATA

BACKGROUND OF THE INVENTION

Field of the Invention

This invention is in the field of breathing rate measurement and oscillometric measurement methods and technology.

Description of the Related Art

Respiration rate (RR), also called "breathing rate", typically expressed in breaths per minute, is an essential but underused vital sign. Jonsdottir et al., in "*Nursing documentation prior to emergency admissions to the intensive care unit*", Nursing in Critical Care•June 2011" reports that although respiratory failures are the most common cause of emergency admissions to ICU, nonetheless respiratory rate is one of the least documented vital signs. This problem is due in part to lack of appropriate breathing rate monitoring equipment.

With the recent worldwide COVID-19 pandemic, adequate methods of assessing respiratory system status have become increasingly important. For example, Xu et al., in *Risk factors for 2019 novel coronavirus disease (COVID-19) patients progressing to critical illness: a systematic review and meta-analysis*, AGING 2020, Vol. 12, No. 12" reports that elderly male patients with a high respiratory rate (along with high body mass index, and other risk factors) are more likely to develop severe COVID-19 infections.

Although a significant amount of prior art exists covering various automated systems and methods for determining respiration rate, to date, as evidenced by the Jonsdottir study, such methods are still lacking. By contrast, consider oscillometric blood pressure monitors, which are now widely available on a low-cost basis. Oscillometric blood pressure monitors are widely available on a non-prescription basis and are in widespread use for home blood pressure monitoring.

Respiration does have an impact on blood pressure measurements. However, to date, efforts to harness oscillometric techniques for respiration rate monitoring purposes have generally been ineffective. Typically, data from multiple physiological sensors (pulse oximeters, multiple cuff devices, non-oscillometric sensors, ECG sensors) has been needed for such devices to function, and such proposals have generally not been met with commercial success. Thus, further advances in this area would be of significant medical importance.

Previous art on oscillometric monitors equipped with additional physiological sensors, such as ECG and pulse oximetry sensors, includes the work of Li, U.S. Pat. No. 10,022,053, the complete contents of which are incorporated herein by reference.

Other automated breathing sensor art includes Dekker, US 2003/0163054; Callahan U.S. Pat. No. 5,094,244; Aung U.S. Pat. No. 5,682,898; Knoll U.S. Pat. No. 10,349,849; Kawamoto 2017/027358, the complete contents of these are incorporated herein by reference.

Academic work in this area includes the work of Chen and Chen, "*A method for extracting respiratory frequency during blood pressure measurement, from oscillometric cuff pressure pulses and Korotkoff sounds recorded during the measurement*" 2016 38th Annual International Conference of the IEEE Engineering in Medicine and Biology Society (*EMBC*)"; other academic work includes the work of Gui et. al., "*Pulse interval modulation-based method to extract the respiratory rate from oscillometric cuff pressure waveform during blood pressure measurement*" Computing in Cardiology (*CinC*) September 2017—ieeexplore.ieee.org.

BRIEF SUMMARY OF THE INVENTION

Breathing causes relatively small changes in an individual's pulse waves, and oscillometric blood pressure monitoring devices can monitor such pulses. However, these breathing rate induced changes are relatively small, and are frequently confounded by noise and artifacts in the oscillometric data. The present invention was inspired, in part, by the insight that if a sufficient number of methods to remove artifacts from oscillometric blood pressure monitor data could be found, then it might be possible to employ more aggressive analytical methods to automatically distinguish the subtle breathing rate signals from the oscillometric pulse rate data.

The present invention was also inspired, in part, on the insight that if the faint breathing signal could be distinguished in different ways (e.g. through their impact on multiple characteristics or dimensions on the dominant pulse wave signal), then each different dimension could be used to verify the accuracy of the other dimension. In other words, if the impact of the patient's or user's respiratory rate could be found to impact multiple observable parameters of the underlying pulse rate signal, then the accuracy of the method would be improved. That is, when the different methods were in agreement, the breathing rate results would be more likely to be accurate. When the different rates were not in agreement, the system could report a warning or an error.

In some embodiments, the invention may be a system, device, and method for automatically determining a breathing rate of a patient. This method is based on analyzing pulse waveforms obtained from an oscillometric device mounted on the patient's limb (often on the patient's wrist). This oscillometric device will often comprise a processor (e.g. microprocessor), air pressure generating and release devices, a pressure sensor, and a built-in inflatable cuff configured to go around the patient's limb. The device will often further comprise a display and/or a wireless transceiver (such as a Bluetooth Low Energy transceiver) for displaying the results. The device may optionally also contain a tri-axial (e.g. three-axis) accelerometer. In some embodiments, a wrist-mounted oscillometric device is preferred.

In addition to operating as a standard oscillometric blood pressure monitor, the device also is configured to analyze the pulse waveforms and to determine artifact-free regions of these pulse waveforms. Here various methods may be used, and the artifact-free or at least artifact-reduced areas of the pulse waveforms may be termed edited pulse waveforms.

To obtain multiple dimensions of breathing rate data, the system makes use of the experimental observation that breathing impacts both the amplitude of the individual pulse waves, as well as the time duration between successive pulse waves (e.g., frequency). These show up as changes in the amplitude of the envelope of the pulse wave signals "AM envelope signals" as well as changes in the frequency of the pulses "FM between-pulse-time signals." The invention determines these AM envelope signals and FM between-pulse-time signals and then determines their AM envelope primary harmonics and FM between-pulse-time main harmonics.

The invention then checks to be sure that the AM envelope primary (or main) harmonics and FM between-pulse-time main harmonic are consistent, and if not, may return a warning or error code. However, if the two results meet consistency criteria, the system will then calculate a weighted function of the AM envelope primary harmonics and FM between-pulse-time main harmonics. These results will then be output (or stored in memory) as the patient's breathing rate (respiratory rate). Alternatively, both AM envelope main harmonics and FM between-pulse-time main harmonics may be used.

BRIEF DESCRIPTION OF THE DRAWINGS

FIG. 9 shows an example of the data used by the invention's pulse percent residual difference (PRD) motion artifact detection algorithm. In this example, the algorithm is detecting that individual pulses 46 and 47 previously shown in FIG. 8, show low correlation with their neighboring pulses.

DETAILED DESCRIPTION OF THE INVENTION

Figure 1:
FIG. 1 shows the invention's wrist-mounted oscillometric device, which unlike prior art devices can also be configured to additionally determine breathing rate data from oscillometric data without use of supplementary physiological sensors such as pulse oximeter or ECG sensors.

FIG. 1 shows an oscillometric device, configured to be mounted on a user's wrist, and configured to also determine breathing rate data (100). Unlike prior art devices, the invention can also be configured to additionally determine breathing rate data from oscillometric data without use of supplementary physiological sensors such as pulse oximeter or ECG sensors. The device contains a plastic enclosure (102), a display (104), control buttons (106) (or the display may be a touch-screen display), and an integrated pressure-cuff (wrist cuff) containing an air bladder (108). Note that the display is showing a pulse rate, systolic and diastolic blood pressure, and also breathing rate in terms of breaths per minute (110).

The high-level mechanical and electrical architectures for the device are illustrated below in FIG. 2 and FIG. 3. Although in some embodiments, the device's electrical circuitry can also support capture of a single lead of Electrocardiography (ECG) and Photoplethysmography (Pulse oximeter or PPG) data for measuring ECG and oxygen saturation ($SpO_2$) as well as pulse wave velocity, an important aspect of the invention is the ability to produce breathing rate information that comes only from one physiological sensor (such as the pressure sensor 122). The use of the accelerometer/gyroscope sensor (202), although present in a preferred embodiment of the invention, is optional.

Figure 2:
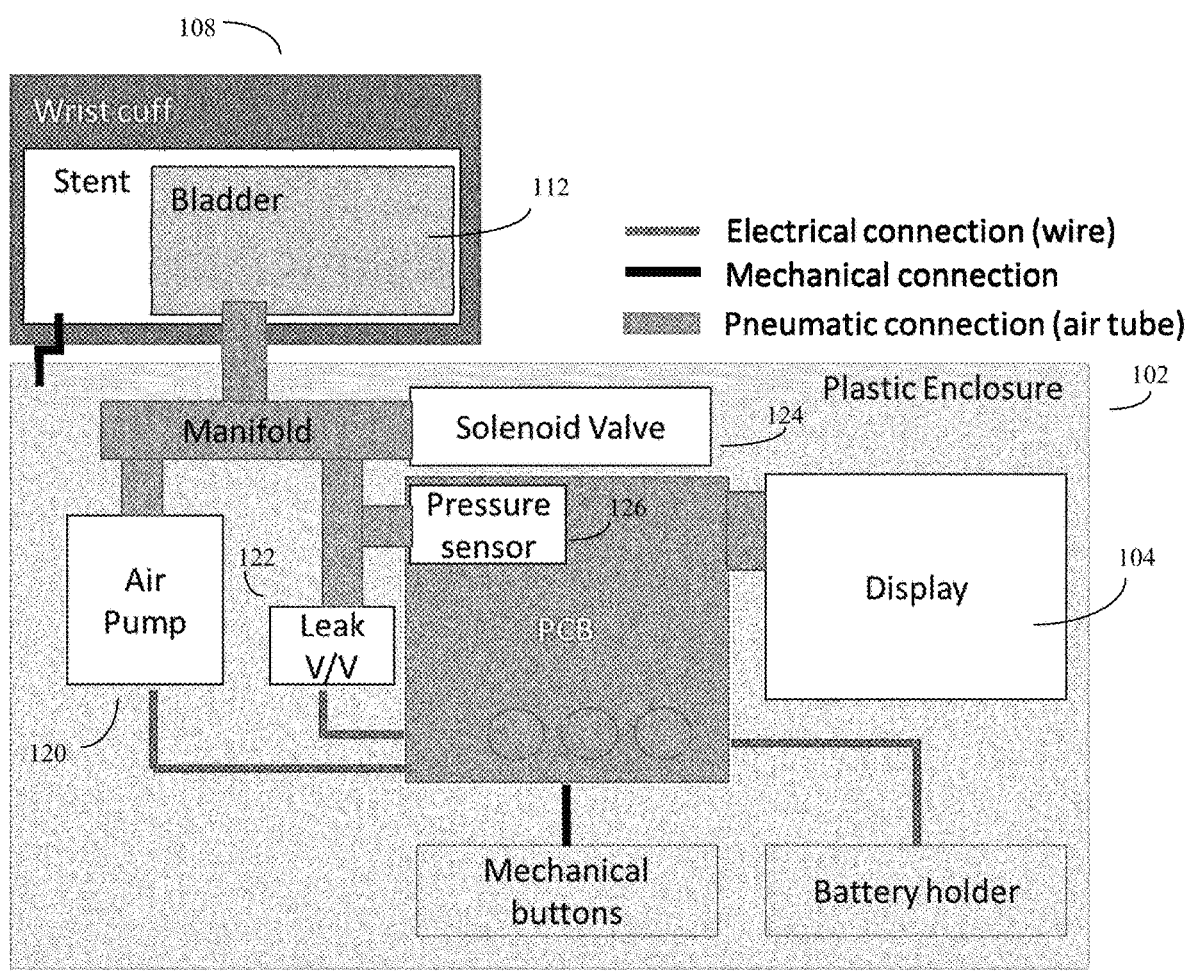
FIG. 2 shows a high-level mechanical architecture drawing of the device.

FIG. 2 shows a high-level mechanical architecture drawing of the device. The device's built-in microprocessor (200) (shown in FIG. 3 as µP), here built into the device's printed circuit board (PCB), receives input from the mechanical buttons and the pressure sensor and controls the operation of the air pump (120) and the solenoid valve (124), and optionally the leak valve (122). (In some embodiments, the leak valve (122) may be a passive leak valve). The device inflates and releases air pressure to and from the device's wrist-cuff air bladder (112) during operation. The air bladder pressure, which fluctuates both according to the inflation status of the bladder, and also in response to the user's pulse waves, is monitored by the pressure sensor (126). Thus, the measurements shown in FIGS. 5-6, 8, 12A, 14, 15-18 are obtained from the pressure sensor (126).

The device's microprocessor also transmits information to the device's display (104), and if the display screen is a touch-sensitive display screen, it can also receive user input from the display. These parts are often at least partially enclosed in the plastic enclosure (102) shown in FIG. 1.

Figure 3:
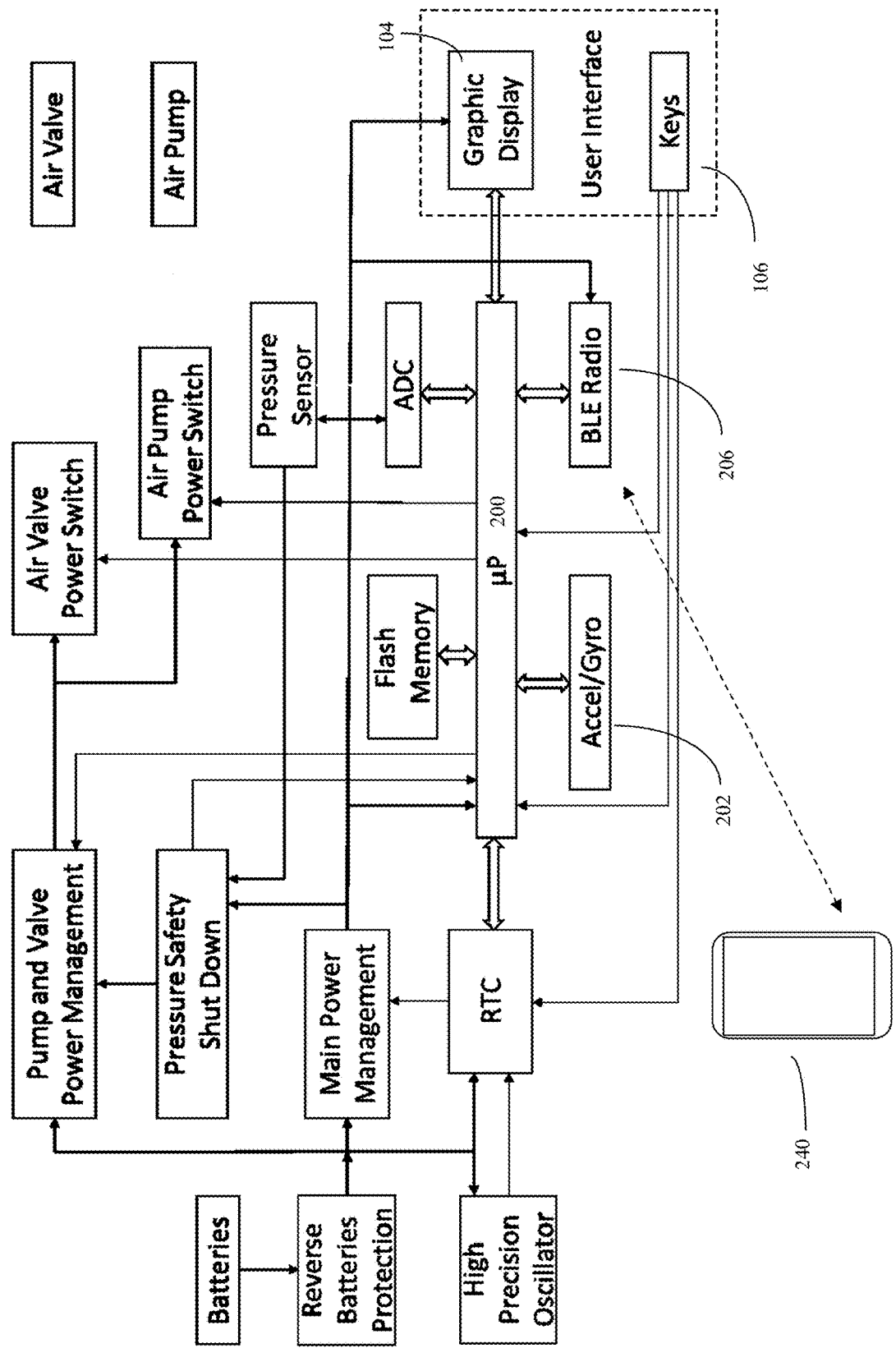
FIG. 3 shows the high-level electrical architecture of the device.

FIG. 3 shows the high-level electrical architecture of the FIG. 1 device. Note that although in this embodiment, the device has an accelerometer/gyroscope sensor, such as a Bosch BMI160 type accelerometer/gyroscope chip (202), which is a motion sensor (non-physiological sensor), this embodiment of the invention need not have other physiological sensors, such as pulse oximeters/PPG sensors and ECG sensors, which are sometimes used in other devices to help obtain breathing rate measurements.

Figure 11:
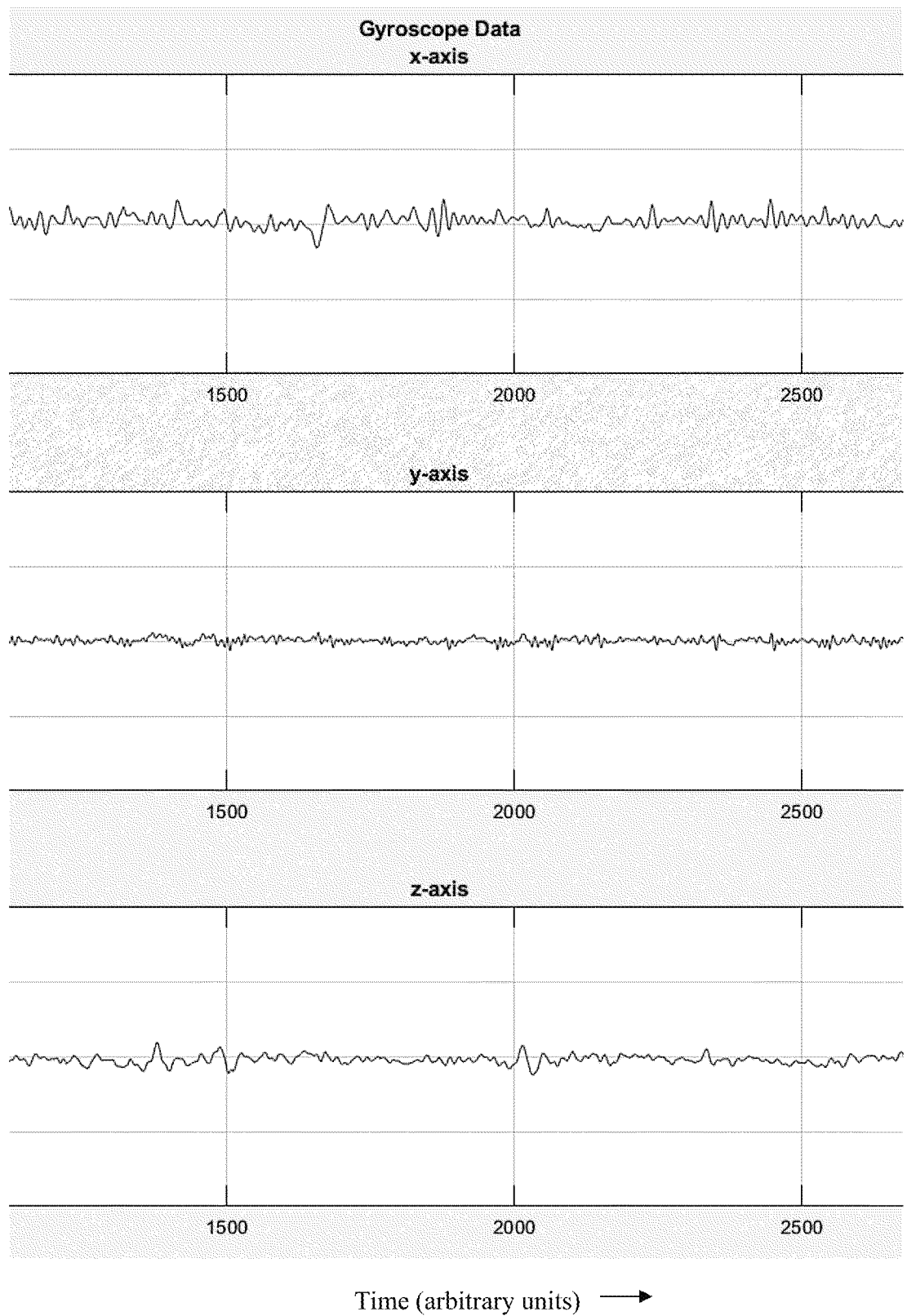
FIG. 11 shows the X, Y, and Z channels of the invention's optional accelerometer/gyroscope sensor showing relatively constant values when this sensor (and the corresponding device) is not moving.
Figure 12A:
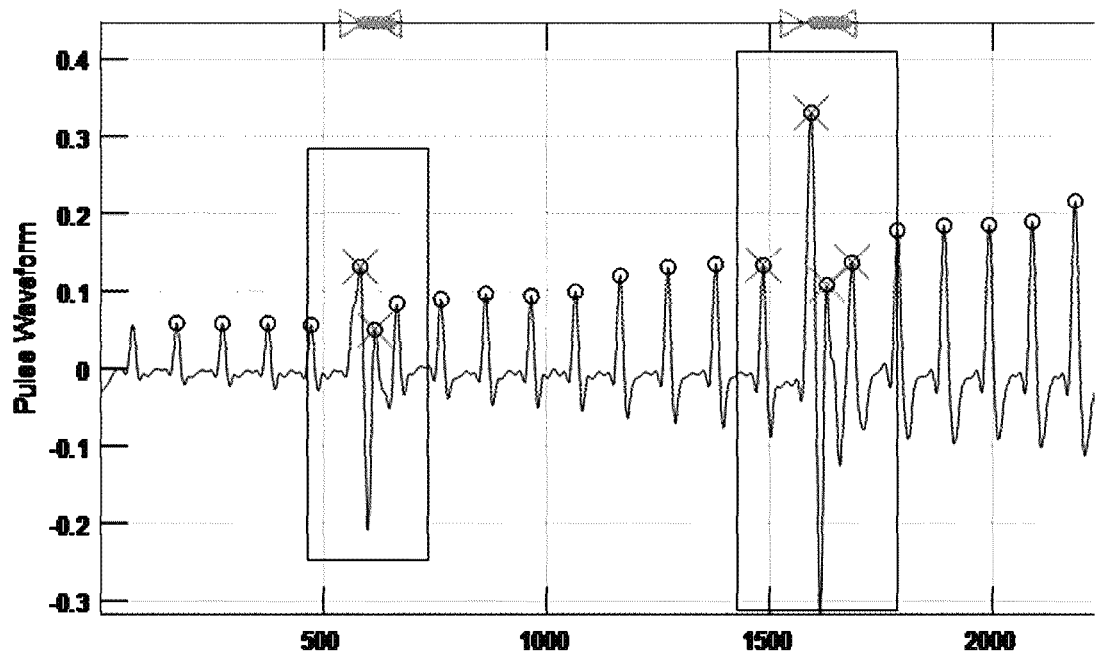
FIG. 12A shows the impact of user wrist movement on the wrist-mounted device during a reading. Such movement can produce pulse waveform artifacts (shown in the boxes).
Figure 12B:
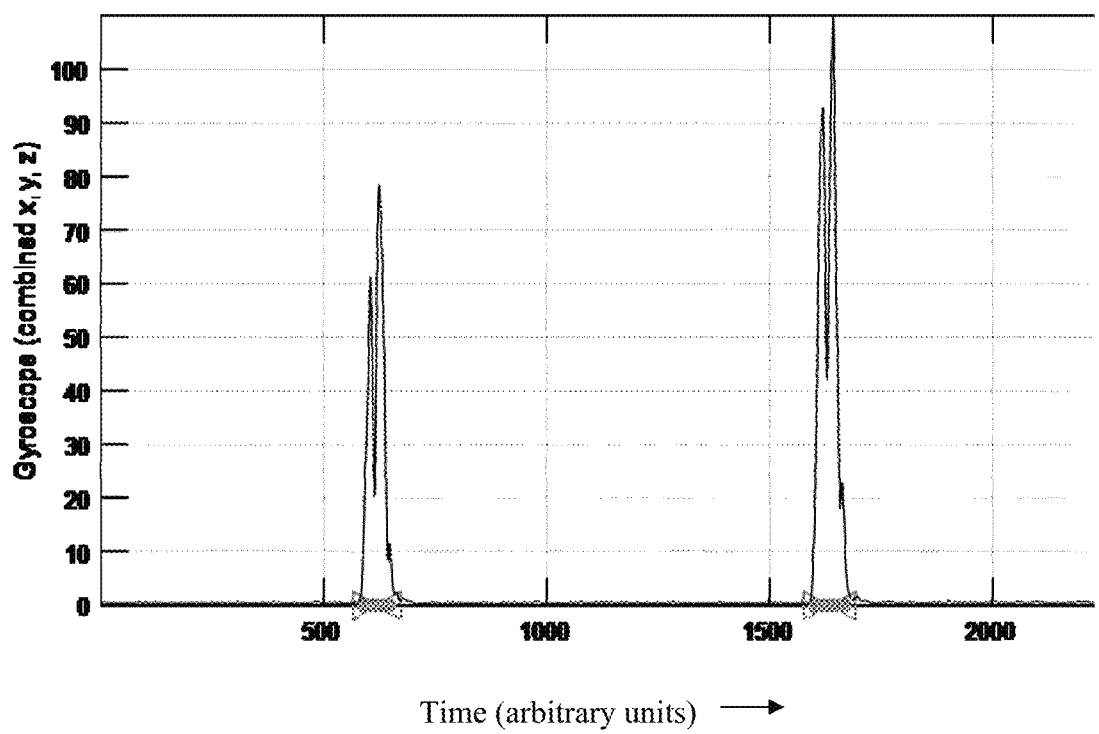
FIG. 12B, which shows the output from the device's optional accelerometer/gyroscope sensor during the same time as FIG. 12A, illustrates how the invention's accelerometer/gyroscope sensor can detect this movement and report the movement to the motion artifact detection algorithm shown in FIG. 13.

The measurements shown in FIGS. 11 and 12B were obtained from the accelerometer/gyroscope chip (202).

Put alternatively, in some embodiments, the device is an oscillometric device that comprises at least one processor (200). This device can optionally further include a display (104) configured to display the user's breathing rate. Alternatively, the device's optional wireless transceivers such as the Bluetooth transceiver (206) (BLE Radio shown in FIG. 3) can transmit this data to an external device such as a smartphone or other suitable wireless device (240).

Figure 4:
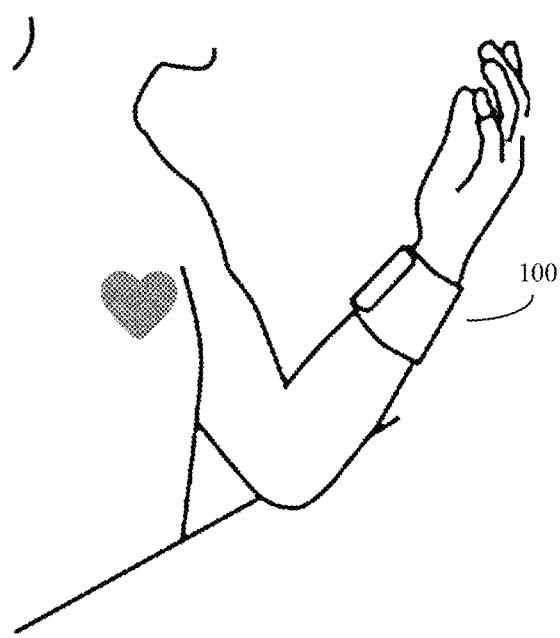
FIG. 4 shows how in in some embodiments, the device may be mounted on the user's wrist and elevated above a surface to approximately the level of the patient's heart.

FIG. 4 shows how in in some embodiments, the device (100) may be mounted on the user's wrist, with instructions to elevate the wrist above a surface to approximately the level of the patient's heart. The patient/user will typically be given instructions to not move their arm during the breathing rate measurement. Here the optional accelerometer/gyroscope sensor (202) is useful to verify that the patient is complying with these instructions. In general, the device may be mounted on a limb of a patient or user, such as the patient's or user's wrist.

One of the reasons why there is little or no prior art on using oscillometric devices to obtain breathing data (at least in the absence of supplementary pulse oximeter data or ECG data) is that the impact of breathing on the oscillometric data is relatively subtle, and is often hidden or obscured by various noise sources. Thus, the present invention relies, in part, on various novel and experimentally determined systems and methods to reduce the noise to the point where the weaker breathing signal can be obtained from the oscillometric data.

System and Algorithm Development

The development of the present invention's system and method relied on clinical testing, and experimentation with alternative devices and alternative algorithms.

As one example of such clinical testing, consider one test which was conducted at Dalhousie Medicine New Brunswick in Saint John, NB, Canada. One test involved a total of 27 healthy participants (6 male, 21 females; aged 22-55, mean±SD=36.6±9.1 years). Experiments were conducted under human ethics approval and written informed consent was obtained from each participant before enrollment.

Auscultatory breathing rate measurements were made by two trained observers using a dual stethoscope, while the device made simultaneous breathing rate measurements during the deflation of the wrist cuff. For each participant, a total of six readings were collected: three non-paced readings (participant breathing naturally) and three paced readings (participant breathing at: 8 breaths/minute, 16 breaths/minute, and 24 breaths/minute). This raw data was then used to evaluate various algorithms. Other experimental tests were also conducted.

As a result of such experimental testing, various aspects of the work were determined on somewhat of a trial and error basis. Certain aspects of the invention, discussed below that were implemented as a result of this trial and error clinical testing include:

Use of accelerometer/gyroscope sensor data for motion artifact detection
Removal of envelope outliers
Variable movement sensitivity based on arm position
Inclusion of a comparison check between "AM" breathing rate determinations and "FM" breathing rate determinations These experimentally determined systems and methods will be discussed in more detail in the following sections.

As previously discussed, in some embodiments, the invention may be a device, system, or method for automatically determining a breathing rate of a patient (or user). Expressing the invention in methods format, this method can comprise various steps. These steps can include obtaining pulse waveforms from an oscillometric device (100) mounted on a limb of the patient or user. These pulse waveforms are then analyzed, using at least one processor, and artifact-free regions of these pulse waveforms are automatically determined, thus obtaining edited (or alternatively weighted and deweighted) pulse waveforms.

The at least one processor (200) will then automatically analyze these edited pulse waveforms. The AM envelope signals and FM between-pulse-time signals of these edited pulse waveforms are then determined. These AM envelope and FM between-pulse-time signals will be defined in more detail shortly. The processor(s) will further analyze these AM envelope signals and FM between-pulse-time signals and determine their AM envelope main harmonics and FM between-pulse-time main harmonics. Then, at least when these AM envelope main harmonics and FM between-pulse-time main harmonics are consistent, the processor(s) will calculate a weighted function of these AM envelope main harmonics and FM between-pulse-time main harmonics, and output (e.g. to a display screen 104, or transmit to another device 240) the result of this weighted function as the breathing rate of the patient/user.

As will be discussed in more detail, to ensure a reliable respiration rate result and a robust algorithm, in a preferred embodiment, automatically edited (artifact-free, or at least artifact reduced) regions of the pulse waveform are used. Regions corrupted by various artifacts (discussed shortly) are typically ignored.

For example, if the level of device movement is significant (too high) such that it will impact the accuracy of the algorithm to an unacceptable extent, the microprocessor (200) is configured to not return a respiration rate result. Instead, it is configured to output an error message.

If, on the other hand, some movement is detected, but the microprocessor determines that movement can be safely ignored, the device may return a respiration rate result, possibly along with a movement warning message, so that the user can be aware that the reported results may have somewhat suboptimal accuracy.

Although, not all versions of the device may comprise a display (104), in a preferred embodiment, the device may utilize a display, such as a thin film transistor (TFT) color display, to provide dynamic user feedback for movement and heart level warnings and errors as well as a real-time visualization of the pulse waveform during reading acquisition.

Experimentally, we have found that the sensitivity of the artifact detection is variable in that it depends on the user's arm position during the reading (see FIG. 4). This arm position can be determined by using the accelerometer/gyroscope sensor data (202) to calculate the forearm angle during a heart level determination algorithm. We have also found that if the user's forearm is raised at an angle, then the pulse waveform tends to be less prone to artifacts due to motion of the user's wrist since the wrist can move freely in the air.

However, if the user's forearm is rested flat on a surface, then the pulse waveform is generally more prone to artifacts due to the motion of the user's wrist since the user's wrist movement has a higher chance of encountering resistance from the surface. Thus, in some embodiments, the sensitivity of the artifact detection may be made variable (e.g., the accelerometer/gyroscope can determine this wrist angle, and vary the motion compensation algorithm accordingly) to accommodate this effect.

Thus, in some preferred embodiments, the oscillometric device will further comprise a tri-axial accelerometer gyroscope device (202). This tri-axial accelerometer gyroscope device will typically report the movement of the oscillometric device to the microprocessor(s) (200). The microprocessor(s) can then use this movement to determine motion artifact-free regions of the user's pulse waveforms for further analysis.

In general, pulse waveform artifacts (and the corresponding artifact-free regions of these waveforms) may be determined by any combination of various techniques, which will shortly be described in more detail. These techniques include using the cuff pressure signal to analyze the waveforms obtained during the cuff deflation (e.g., the deflation curve) by using the cuff pressure sensor (126) signal. Other techniques also include analysis of pulse cross-correlations using the cuff pressure signal, analysis of envelope outliers using the cuff pressure signal, and analysis of the tri-axial accelerometer/gyroscope signal.

More specifically, in some embodiments, the artifact-free regions of the pulse waveforms can be automatically determined by obtaining oscillometric cuff deflation signals, and analyzing these cuff deflation signals for areas where neighboring pulses exhibit below average cross-correlation. Alternatively, or additionally the device can use the tri-axial accelerometer/gyroscopic signals from the sensor (202) to automatically de-weigh (e.g. remove, or deemphasize) those cuff deflation signals obtained during the time in which the tri-axial accelerometer/gyroscope detects motion above a preset threshold. As yet another option, the invention may edit the envelope of the pulse waveforms, and automatically de-weigh (e.g., remove or deemphasize) the pulse waveform data associated with envelope outliers above a preset threshold.

Figure 5:
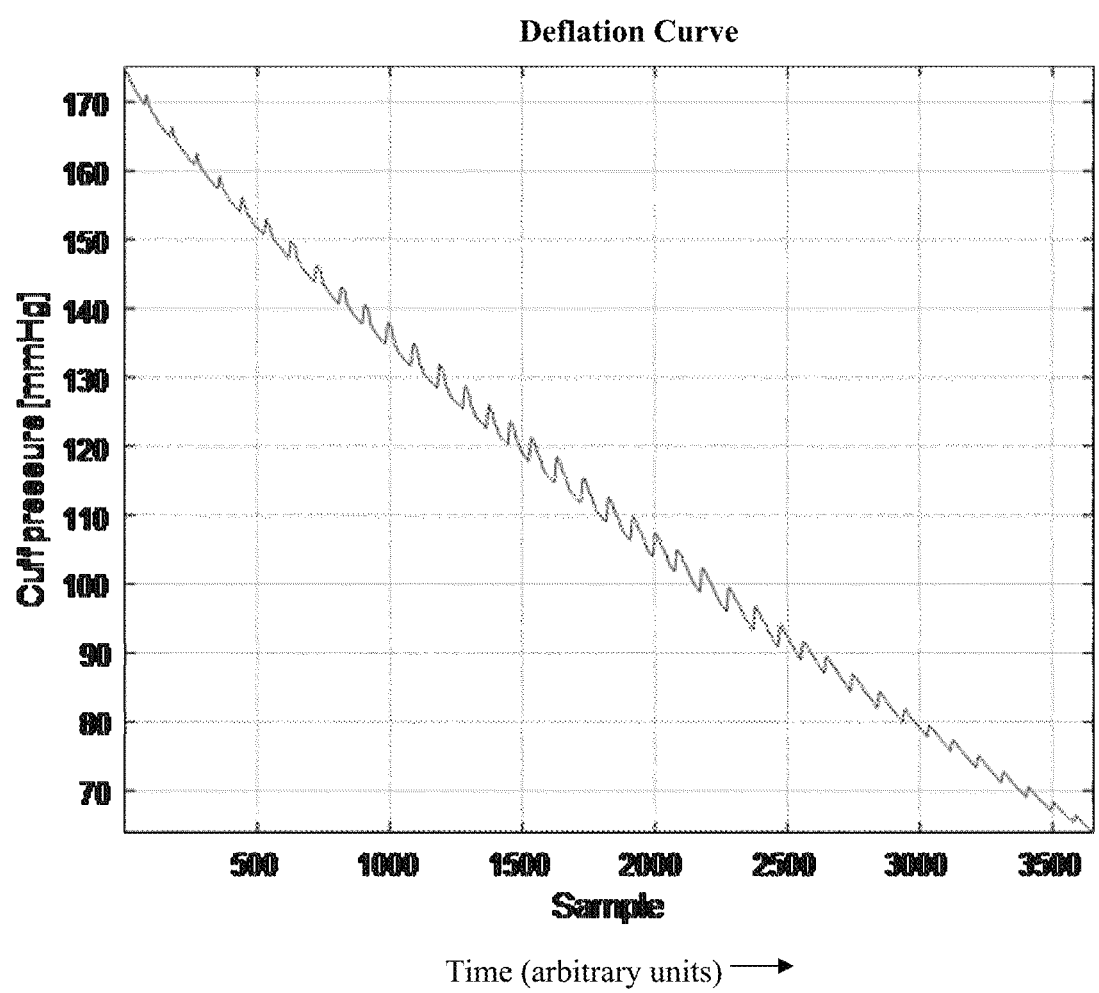
FIG. 5 shows an example of a cuff pressure signal waveform that can be obtained while the cuff deflates.

FIG. 5 shows an example of a cuff pressure signal waveform that can be obtained while the cuff deflates.

Figure 6:
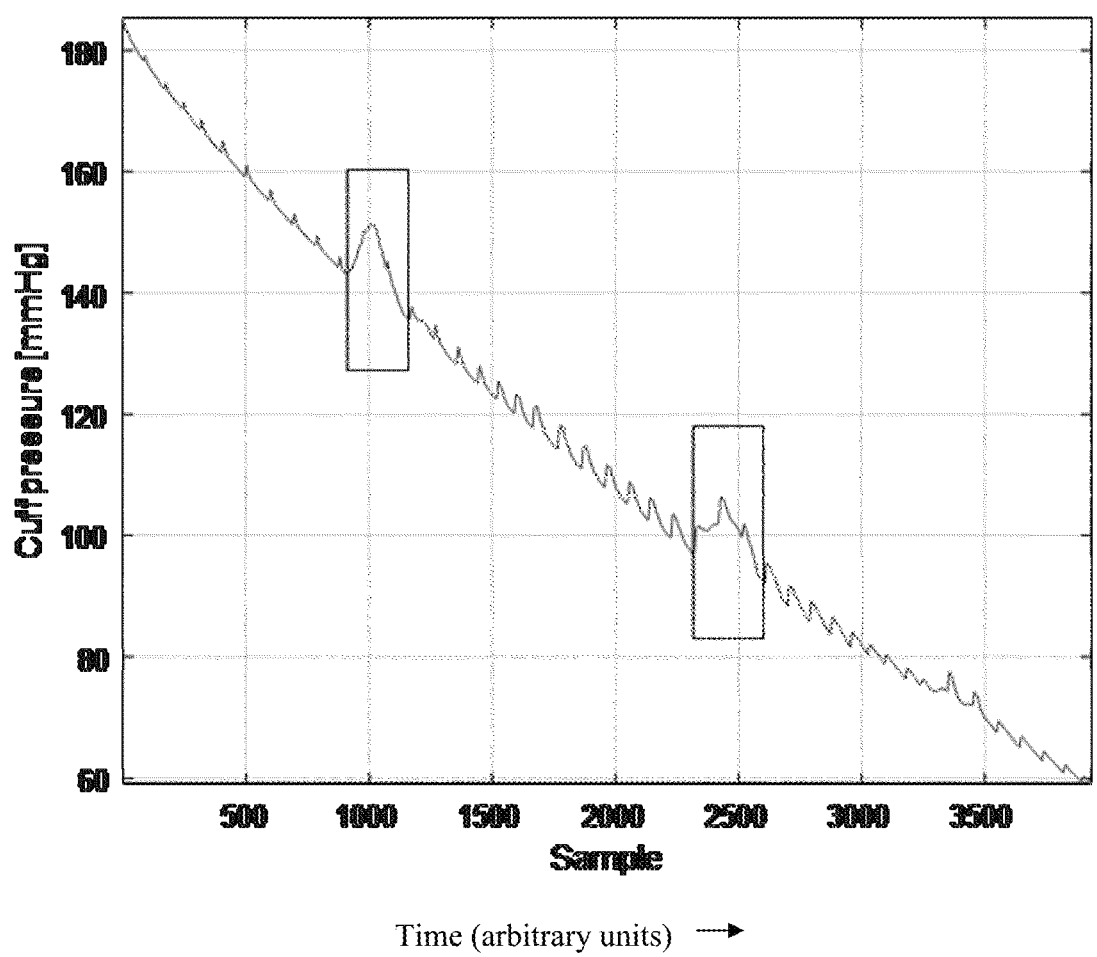
FIG. 6 shows an example of a cuff pressure signal obtained while the cuff is deflating. In this example, the signal also contains motion artifacts, shown in the two boxes.

FIG. 6 shows an example of a cuff pressure signal obtained while the cuff is deflating. In this example, the signal also contains motion artifacts, shown in the two boxes.

Figure 7:
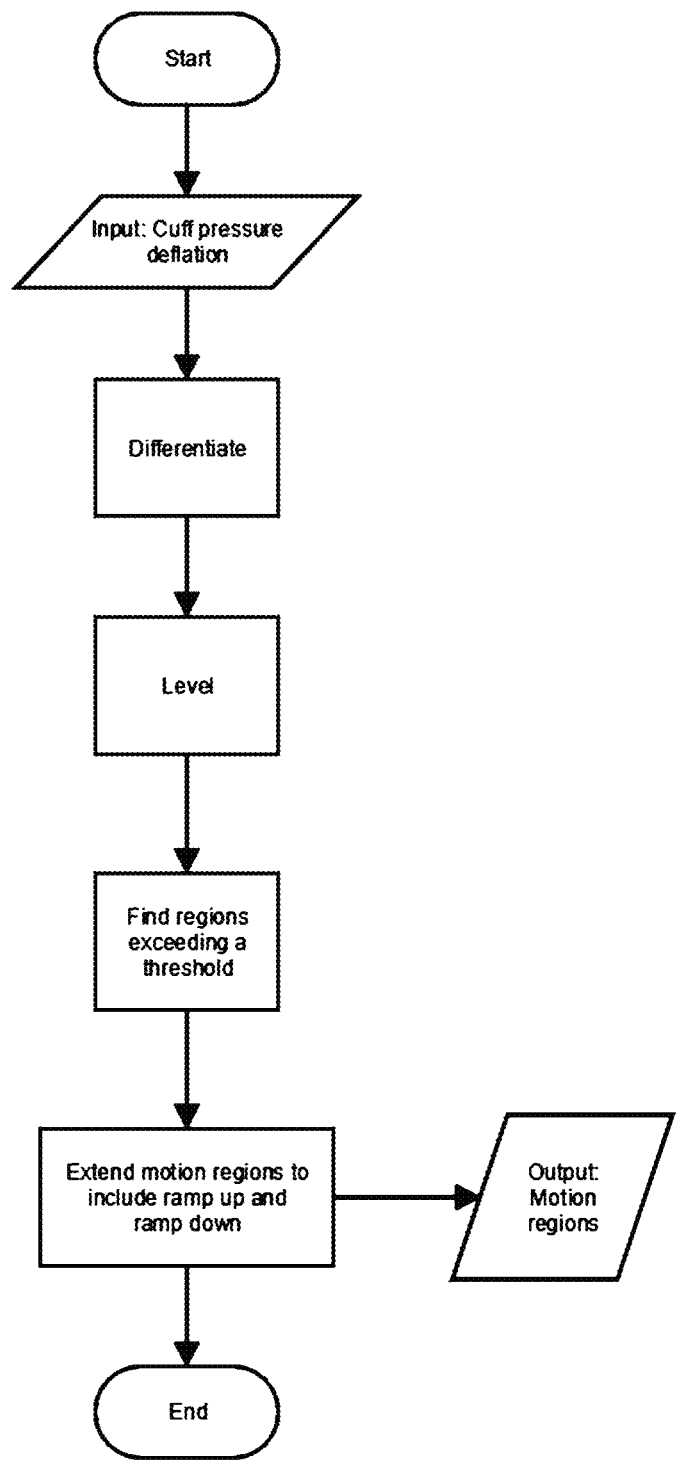
FIG. 7 shows a flowchart of one embodiment of the cuff pressure artifact detection algorithm.

FIG. 7 shows a flowchart of a cuff pressure artifact detection algorithm. Note that in the signal shown in FIG. 6, there is a high-frequency component, caused by the user's individual heartbeat pulses (e.g. one pulse per heartbeat). There is also a low-frequency component, caused by the gradual deflation of the device's cuff. (This gradual deflation is controlled by the device's processor 200, and the leak valve 122).

There are also intermediate frequency deviations, shown in the FIG. 6 boxes, where the cuff pressure data quickly rises above the expected low-frequency deflation curve threshold and then falls back. These can be determined by (in FIG. 7) configuring the processor (200) to differentiate the signal (optionally after a high pass filter to block the high-frequency component) and to look for regions (corresponding to the boxes in FIG. 6), where the rate of change exceeds an expected threshold. This allows the system to automatically "cut out" the suspicious data, and focus on the regions outside of boxes in FIG. 6. This is one type of edited pulse waveform data.

Determining other types of motion through analysis of the deflation curve using the cuff pressure signal: As shown in FIG. 5, the deflation curve is the waveform representing a decreasing cuff pressure signal. The user's pulse causes small deviations in the pressure, which is detected by the pressure sensor (126). These small pulse pressure "blips" contain blood pressure information. According to the invention, when outside noise is removed, these small blips also contain patient/user breathing rate information.

Unfortunately, the accelerometer/gyroscope signal cannot capture all types of hand motion artifacts. For example, the movement of the user's fingers may not always be captured by the accelerometer/gyroscope (202) because there is insufficient motion of the device (100) itself. However, we have found this type of patient/user finger movement can be detected because it creates predictable medium-scale artifacts in the deflation curve (see FIG. 6).

To detect this type of patient/user type of finger movement, shown in the boxes in FIG. 6, the processor can first use a lowpass filter to smooth the deflation curve and filter out (remove) the higher frequency radial pulse component of the signal. The lower frequency, but large amplitude, finger motion artifacts are unlikely to be removed by this low frequency filter. These finger motion artifacts can be detected as artifacts in the smoothed deflation curve. The finger motion artifacts, for example, will show up in the derivative of the smooth deflation curve. That is, the derivative of the overall deflation curve is nearly a constant, while the finger motion artifacts show up as changes in this derivative, and these can be automatically detected by the device's microprocessor. The microprocessor then knows to edit out these pulses, or at least deweigh those pulses in the boxed regions because they are at risk of having been distorted by finger motion.

A flowchart of this type of cuff pressure artifact detection algorithm is shown in FIG. 7.

Detection of "subtle" artifacts by analysis of pulse cross-correlations using the cuff pressure signal: Unfortunately, some types of remaining artifacts are too subtle to be detected by either the accelerometer/gyroscope signal or by using the deflation curve to detect additional types of motion.

Figure 8:
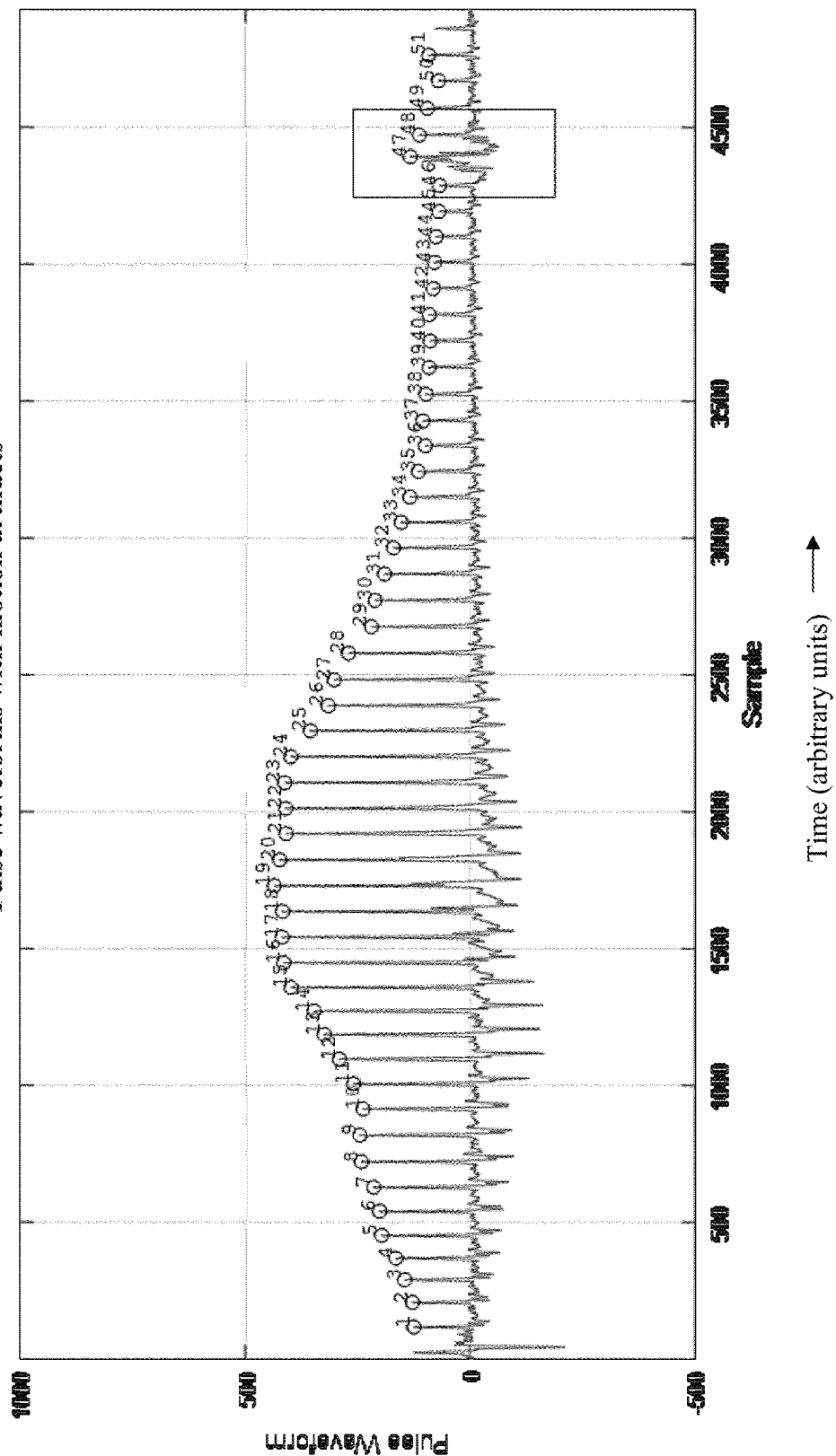
FIG. 8 shows an example of a pulse waveform. In this example, both pulse 46 and pulse 47 (shown in the box) contain motion artifacts. These can occur when the user moves their hand (see FIG. 4) during the breathing rate assessment.

As shown in FIG. 8, however, these "subtle" or "residual" artifacts may still corrupt the pulse waveform. To find these "subtle" or "residual" artifacts, the invention can use another technique that operates by determining the amount of cross-correlation between individual pulses. Through experimental work, we have found that both pulses with motion artifacts, and other types of "subtle" problems as well, exhibit a low correlation to other pulses throughout the waveform. This is shown in FIG. 9.

Figure 9:
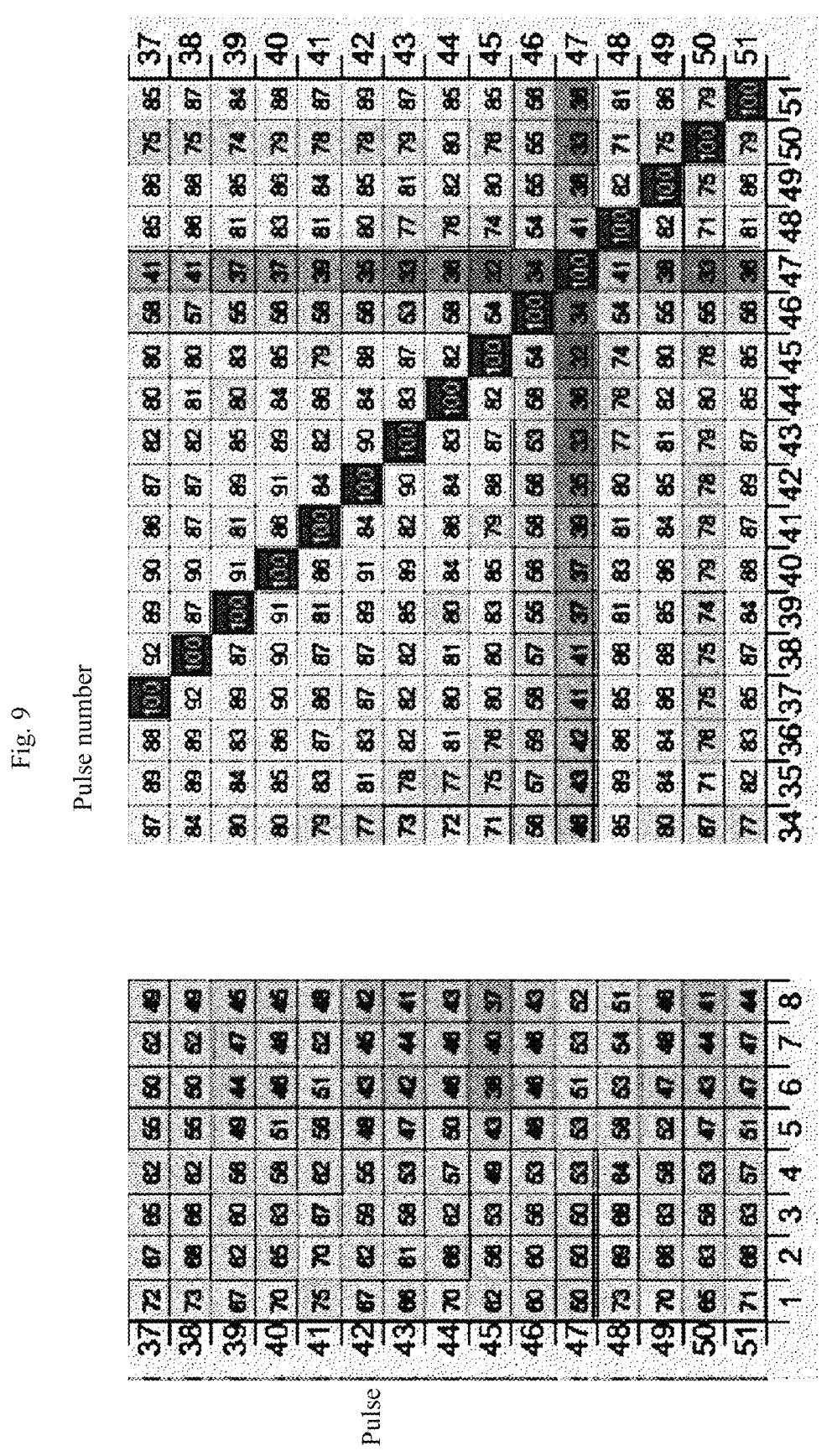

FIG. 9 shows an example of the data used by the invention's pulse percent residual difference (PRD) motion artifact detection algorithm. The numbers within the matrix are the modified PRD values that are calculated and which indicate the cross-correlation between pulses. In this example, the algorithm is detecting that individual pulses 46 and 47 previously shown in FIG. 8, show low correlation with their neighboring pulses. Here the percent correlation between neighboring pulses is shown in numbers, and significant differences are also shown in contrasting shades, forming a "cross pattern" centered on the intersection of pulse 47 with itself. Note that although an individual pulse will correlate 100% with itself, it will usually also correlate about 80-90% with its neighboring pulses. By contrast, Pulse 47 only correlates in the 30-40% range with its neighbors, and pulse 46 only correlates in the 50% range with its immediate neighbor pulses.

Here, according to the invention, the processor(s) computes these correlations using a modified percent residual difference (PRD) formula. This modified PRD formula enables a more sensitive measure of comparison than the more conventional Pearson correlation coefficient. A flowchart showing one embodiment of the invention's pulse PRD based artifact detection algorithm is shown in FIG. 10.

Figure 10:
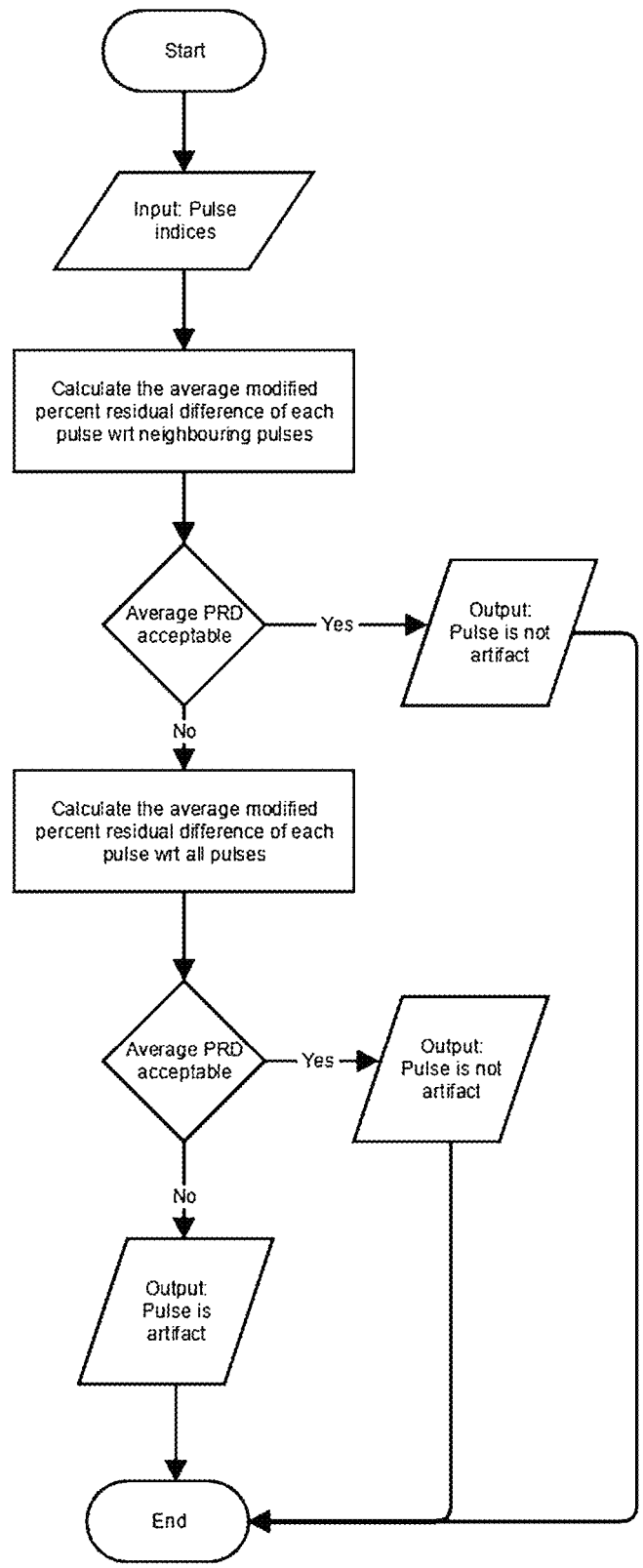
FIG. 10 shows a flowchart of the invention's pulse percent residual difference (PRD) motion artifact detection algorithm, which operated on the data previously shown in FIG. 8 and FIG. 9.

FIG. 10 shows a flowchart of the invention's modified pulse percent residual difference (PRD) motion artifact detection algorithm, which operates on the data previously shown in FIG. 8 and FIG. 9. Note that if the modified percent residual difference (PRD) is too high (see FIG. 8 and FIG. 9), this algorithm will determine that the output pulse is likely an artifact, and will thus either exclude this data and/or generate an error message.

Regarding analysis of the tri-axial accelerometer/gyroscope signal: In a preferred embodiment, the device's optional accelerometer/gyroscope sensor (here a Bosch BMI160) provides three channels of motion (accelerometer) data and three channels of gyroscopic data) representing motion in and around the x, y, and z axes. Generally, either a three-axis accelerometer or a three-axis gyroscopic sensor can work. When there is no movement of the device (100) during a reading, these data are relatively passive, i.e., low amplitude and flat. This is shown in FIG. 11. FIG. 11 shows the X, Y, and Z channels of the gyroscope sensor showing relatively constant values when the sensor is not moving. Note that the accelerometer/gyroscope sensor does not report data on the patient's physiological state.

According to the invention, at least some types of patient/user wrist movement during a breathing rate reading can be detected through the accelerometer/gyroscope data. This is shown in FIG. 12A and FIG. 12B.

FIG. 12A shows the impact of user wrist movement on the wrist-mounted device during a reading. Such movement can produce pulse waveform artifacts (shown in the boxes). FIG. 12B, which shows the output from the device's optional accelerometer/gyroscope sensor during the same time as FIG. 12A, shows how the invention's accelerometer/gyroscope sensor can detect this movement and report the movement to the motion artifact detection algorithm shown in FIG. 13.

Figure 13:
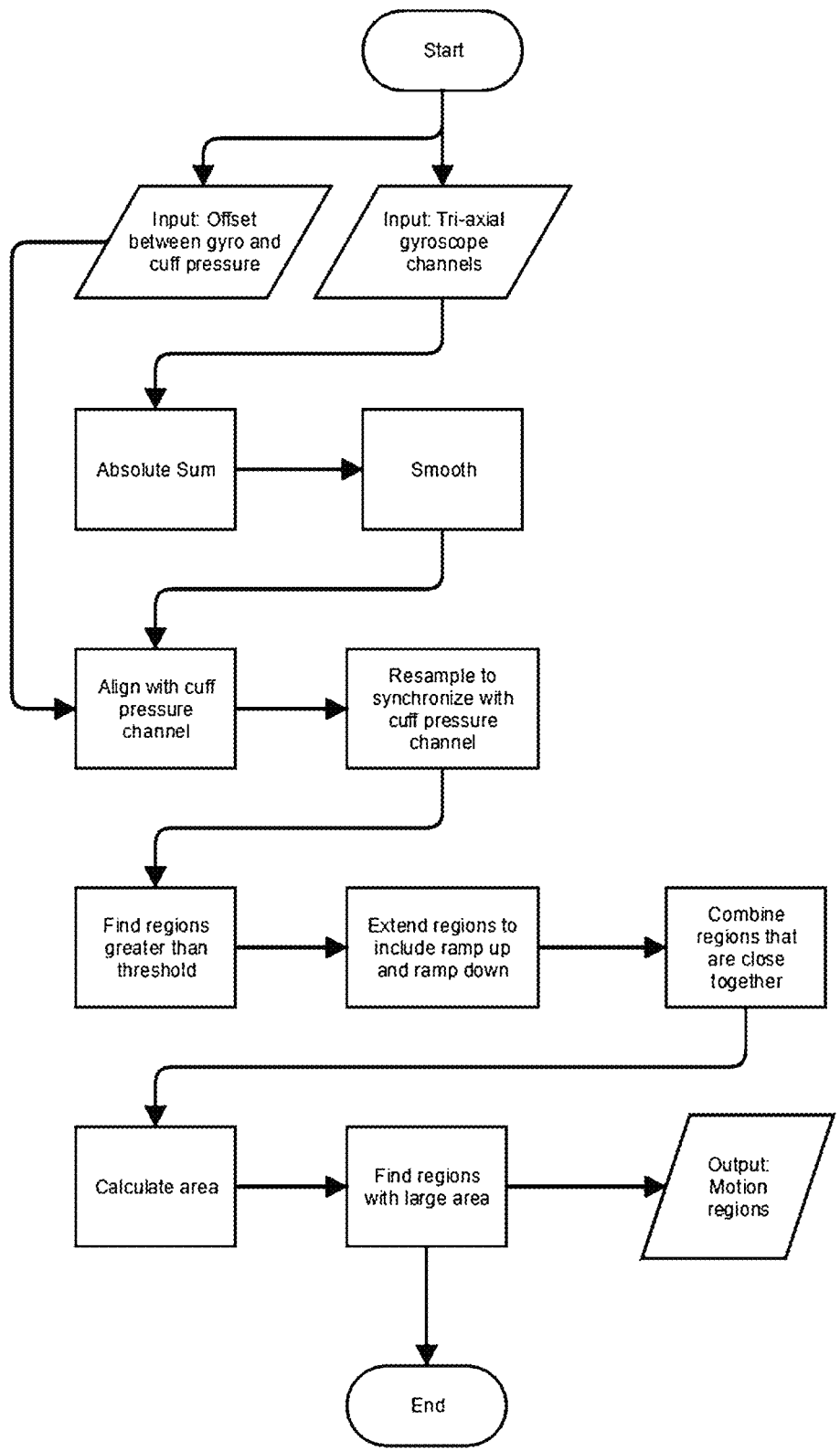
FIG. 13 shows a flowchart of the invention's accelerometer/gyroscope motion artifact detection algorithm.

FIG. 13 shows a flowchart of the invention's accelerometer/gyroscope motion artifact detection algorithm. This algorithm can take input from the oscillometric detector (FIG. 12A) and the accelerometer/gyroscope sensor (FIG. 12B) and output the motion free regions of the signal where good data can be obtained.

Figure 14:
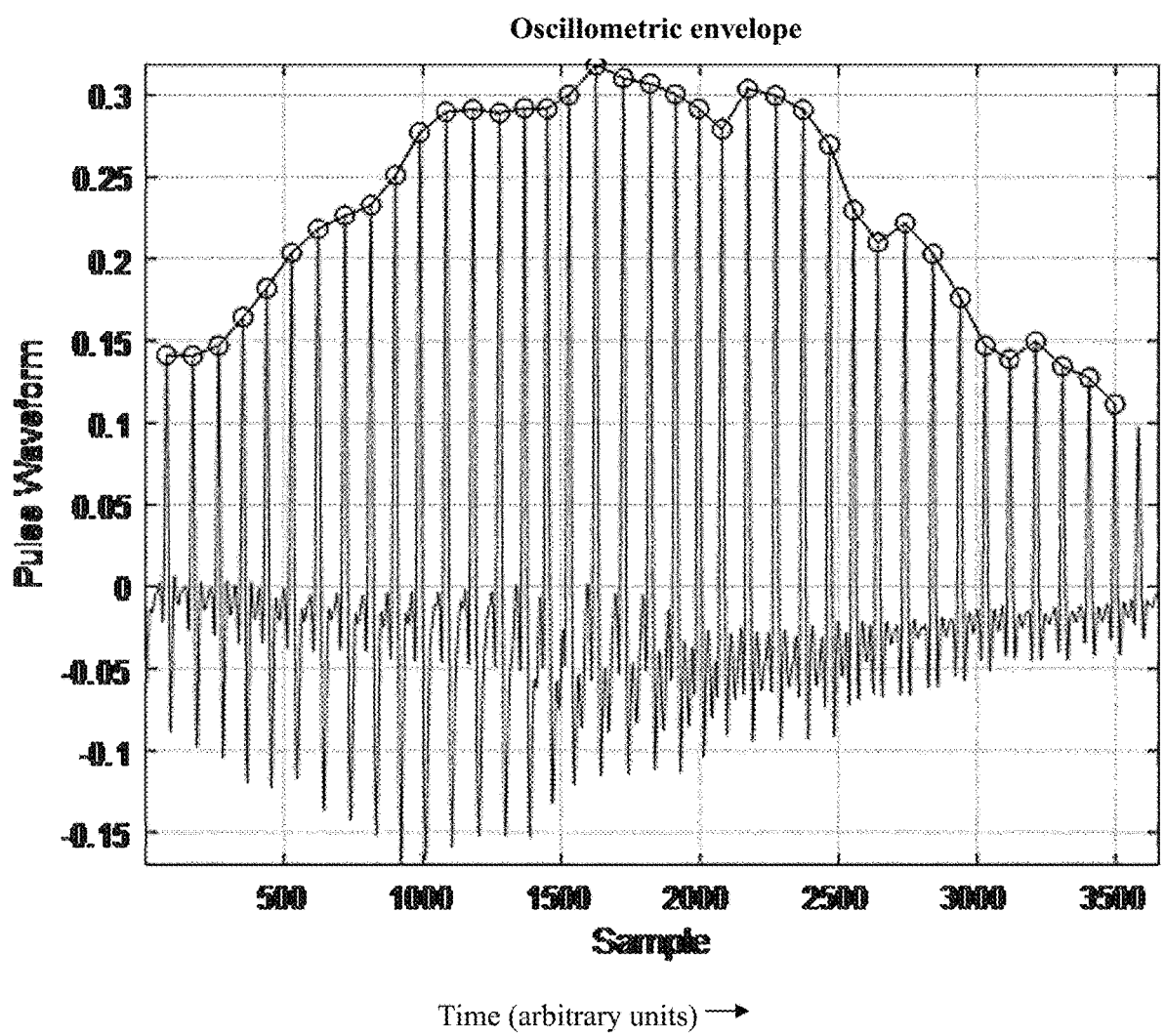
FIG. 14 shows how the user's pulse waveforms fit within an oscillometric envelope.

Other error detection algorithms—analysis of envelope outliers using the cuff pressure signal: Other algorithms may also be used to detect certain types of errors. For example, as shown in FIG. 14, the envelope of the pulse waveform exhibits a gradual rise and fall as the cuff pressure deflates from above the systolic blood pressure to below the diastolic blood pressure. However, certain pulses may not follow this expected behavior. Some pulses, for example, may instead exhibit a higher or lower than expected amplitude. In some embodiments of the invention, these "envelope outliers" can also be automatically detected and removed in order to prevent these envelope outliers from impacting the overall shape of the envelope.

FIG. 14 shows how the user's pulse waveforms fit within an oscillometric envelope. Notice the gradual rise and fall of the envelope. In some embodiments of the invention, to further reduce artifacts, individual pulses that do not adhere to this gradual slope can also be excluded by an appropriate error detection algorithm.

Thus, the invention uses multiple and redundant error detection methods to remove artifacts from the pulse wave signal. Due to this redundancy, although use of accelerometer/gyroscope sensor data to assist in error analysis is preferred, the system can also operate without use of the accelerometer/gyroscope sensor.

"AM" and "FM" Analysis Methods:

As previously discussed, according to the invention, in at least some embodiments, the processor(s) determines the previously discussed "AM envelope signals" and "FM between-pulse-time signals" by determining an oscillometric envelope of pulse peak amplitudes and times between individual pulses of the pulse waveforms. Here, we will discuss these techniques in more detail.

According to the invention, the "AM" signal is based on pulse peak amplitudes, that is, the oscillometric envelope of the pulse waveform.

By contrast, the "FM" signal is the instantaneous pulse rate signal (pulse rate per pulse), which is based on the timing of the individual pulse positions with respect to each other. These signals are extracted from the identification of pulses in the processed cuff pressure signal.

AM methods: Note that the envelope of the pulse waveform exhibits a gradual rise and fall as the cuff pressure deflates from above the systolic blood pressure to below the diastolic blood pressure (see FIG. 8). This is referred to as an oscillometric envelope. As the user breathes, the change in chest volume caused by air entering and exiting the lungs impacts the amplitude of the pulse acquired by the device. This mechanical influence of breathing causes a rise and fall in the pulse amplitude and is modulated within the oscillometric envelope. This is referred to as the amplitude modulation (AM) breathing signal (see FIG. 15). This name was chosen because the underlying method is somewhat analogous to AM radio in that information (i.e., breathing) is stored in the form of amplitude changes.

FM methods: As the user breathes, a natural phenomenon known as respiratory sinus arrhythmia impacts the pulse duration (e.g., time between neighboring pulses). This electrical influence of breathing causes an increase and decrease in the pulse frequency. This doesn't necessarily impact the amplitude of the oscillometric envelope, but does impact the time between successive pulse waves within the oscillometric envelope. This different effect has been named the "frequency modulation (FM)" breathing signal (see FIG. 16). It was given this name because this effect is somewhat analogous to FM radio. That is, here, the breathing rate information is stored in the form of frequency changes (e.g., times between successive pulse waves).

Figure 15:
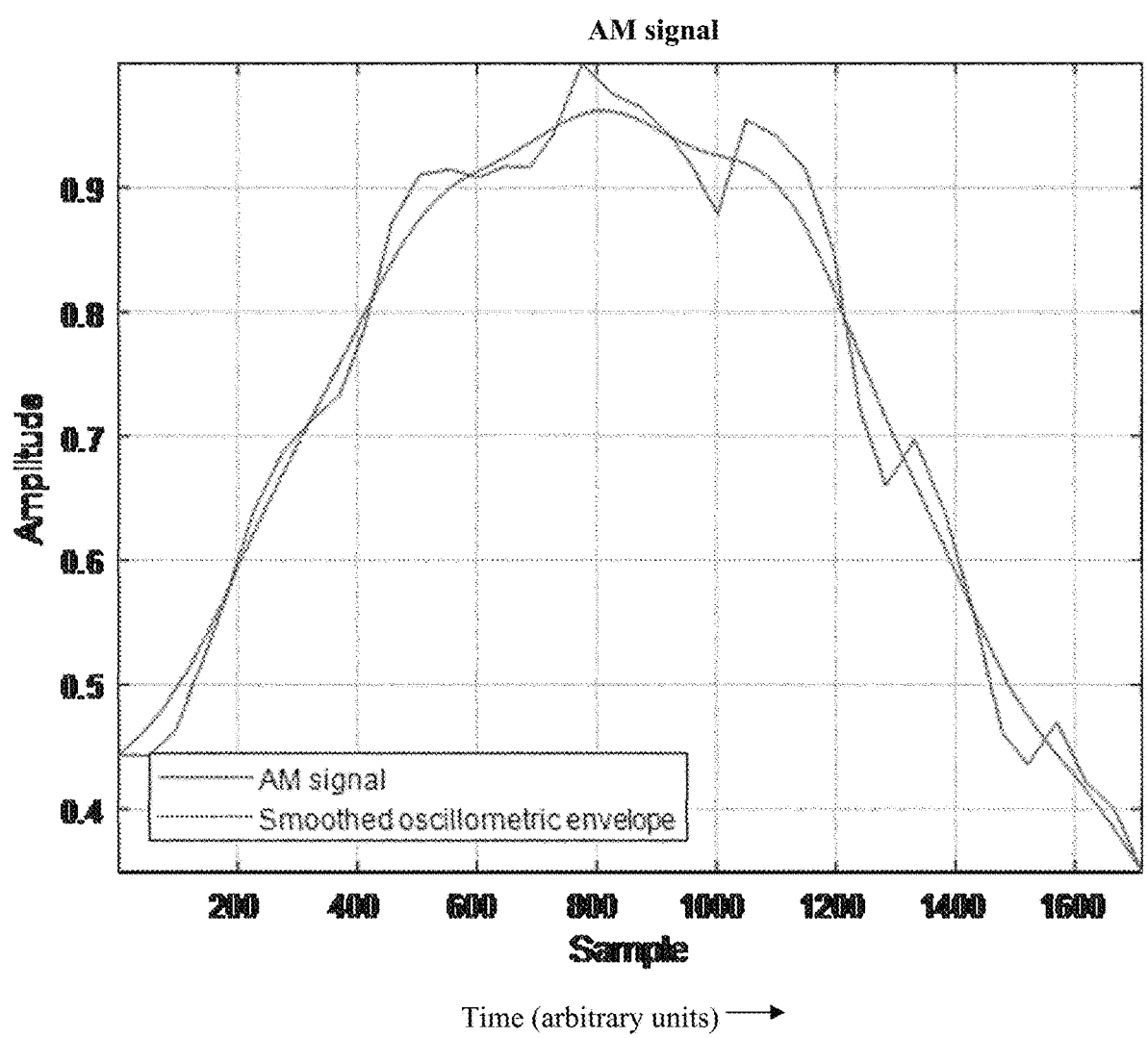
FIG. 15 shows the invention's "amplitude modulation" (AM) type breathing signals.

FIG. 15 shows the invention's "amplitude modulation" (AM) type breathing signals. In this figure, the invention's AM signal both rises above and falls below the smoothed oscillometric envelope. This rise and fall of amplitudes (e.g., deviation from the smoothed envelope) is caused by the mechanical influence of the user's chest motions during breathing. This is, in essence, one type of "breathing rate" signal, which can often be obscured unless at least some of the various previously described artifacts are removed.

Figure 16:
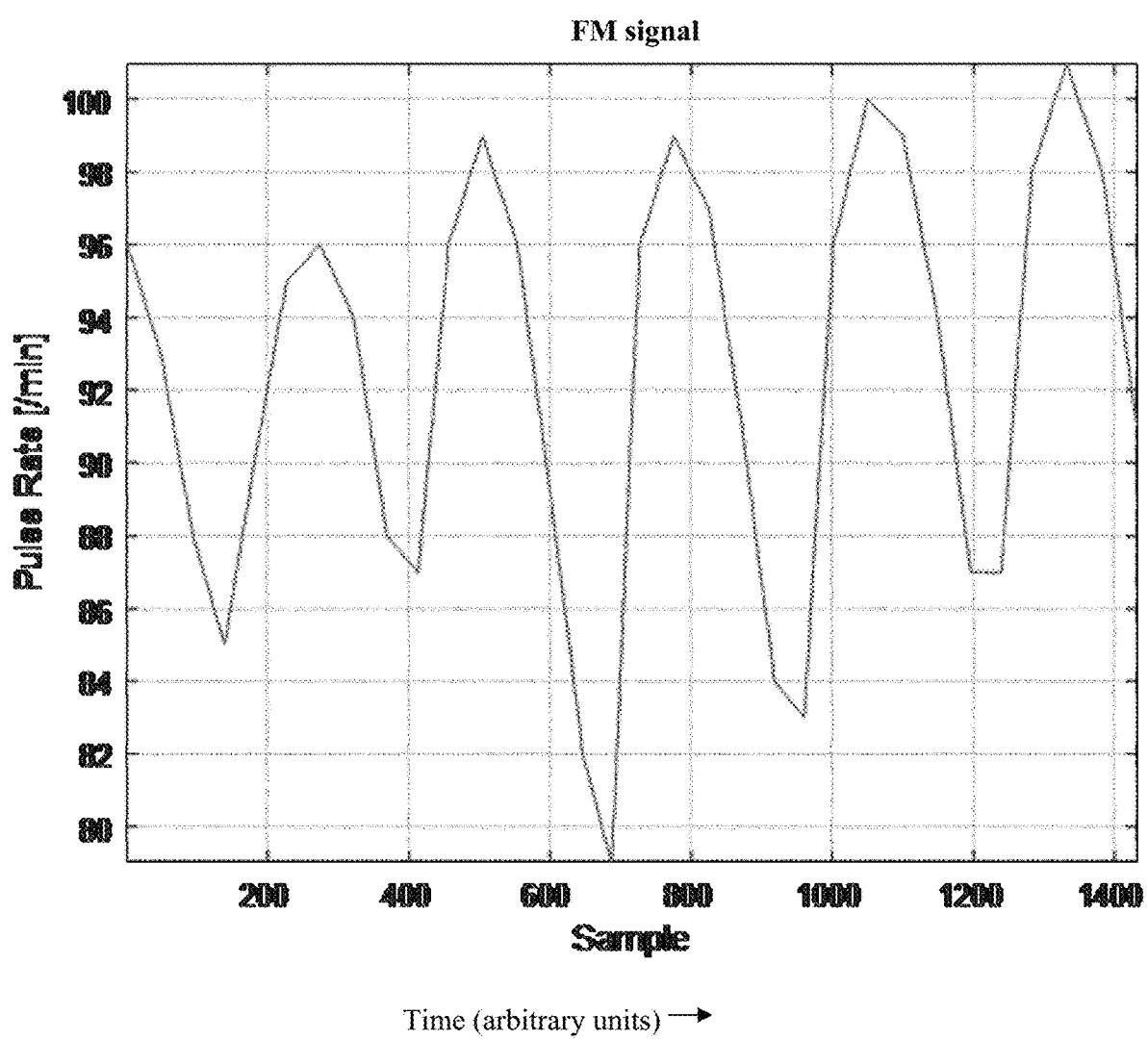
FIG. 16 shows an example of the invention's "frequency modulation" (FM) type breathing signal.

FIG. 16 shows an example of the invention's "frequency modulation" (FM) type breathing signal. The instantaneous pulse rate (e.g., time difference between successive pulses) rises and falls throughout the pulse waveform. This rise and fall of frequencies are associated with the electrical influence of breathing. In other words, during one phase of respiration, the pulses occur quicker together in time, while in a different phase of respiration, the different pulses occur slower in time. This is a second type of "breathing rate" signal that can often also be obscured unless at least some of the various previously described artifacts are removed.

Thus, in some embodiments, the processor(s) further determines the FM between-pulse-time signals by computing time differences between peak indices of the pulse waveforms and using these time differences to calculate instantaneous pulse rates of the patient/user. The processor can then use these instantaneous pulse rates to determine the FM between-pulse-time signals.

Further, in some embodiments, the processor determines the AM envelope main harmonics and FM between-pulse-time primary harmonics by computing a Fourier transform of the oscillometric envelope of the pulse waveform; and calculating a Fourier transform or power spectral density of the FM between-pulse-time signals (e.g., determine the primary/main harmonics by assessing an instantaneous pulse rate signal based on the pulse positions with respect to each other).

More specifically, the main harmonics of the AM and FM signals can be determined through frequency-domain analysis (such as, power spectral density). Here, the time-domain representations of the AM and FM signals are shown in FIG. 15, and FIG. 16, respectively.

According to the invention, the patient's or user's respiration rate can be derived from the main harmonic of each of these waveforms. The main harmonic, which is an indication of the highest-amplitude frequency, can be determined by converting the time-domain waveforms to their frequency-domain representations. This can be done by various methods, including the Fourier transform, using a power spectral density (PSD) estimate via Welch's method, and other methods. Once this is done, the processor then automatically determines the frequency with maximum power in the range of interest (e.g., within physiological breathing rate ranges).

Figure 17:
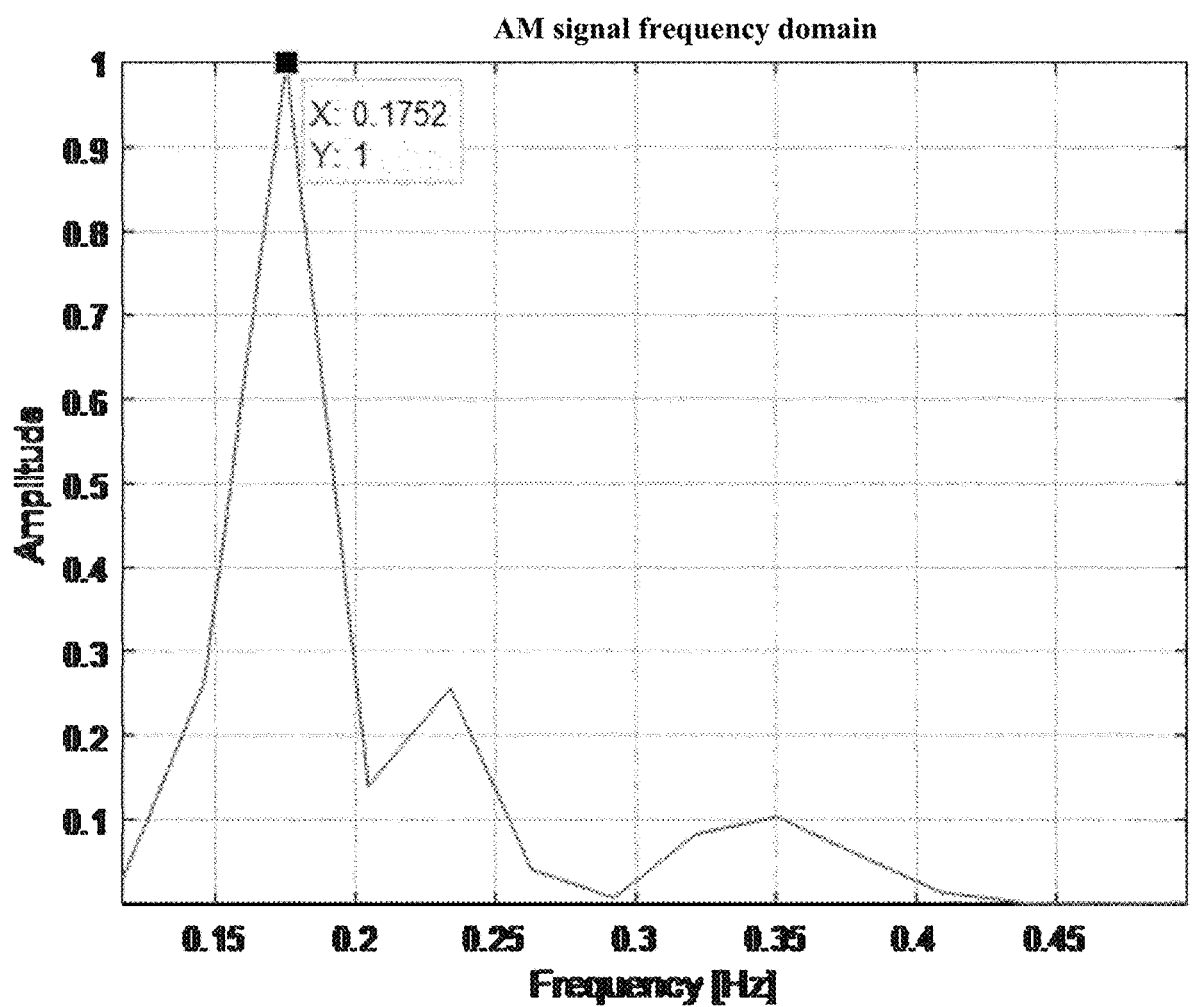
FIG. 17 shows a frequency-domain representation of the amplitude modulation (AM) breathing signal from FIG. 15.

FIG. 17 shows a frequency-domain representation of the amplitude modulation (AM) breathing signal from FIG. 15. The main harmonic can be seen as 0.1752 Hz, which is an AM signal calculated breathing rate of 10.51 breaths per minute.

Figure 18:
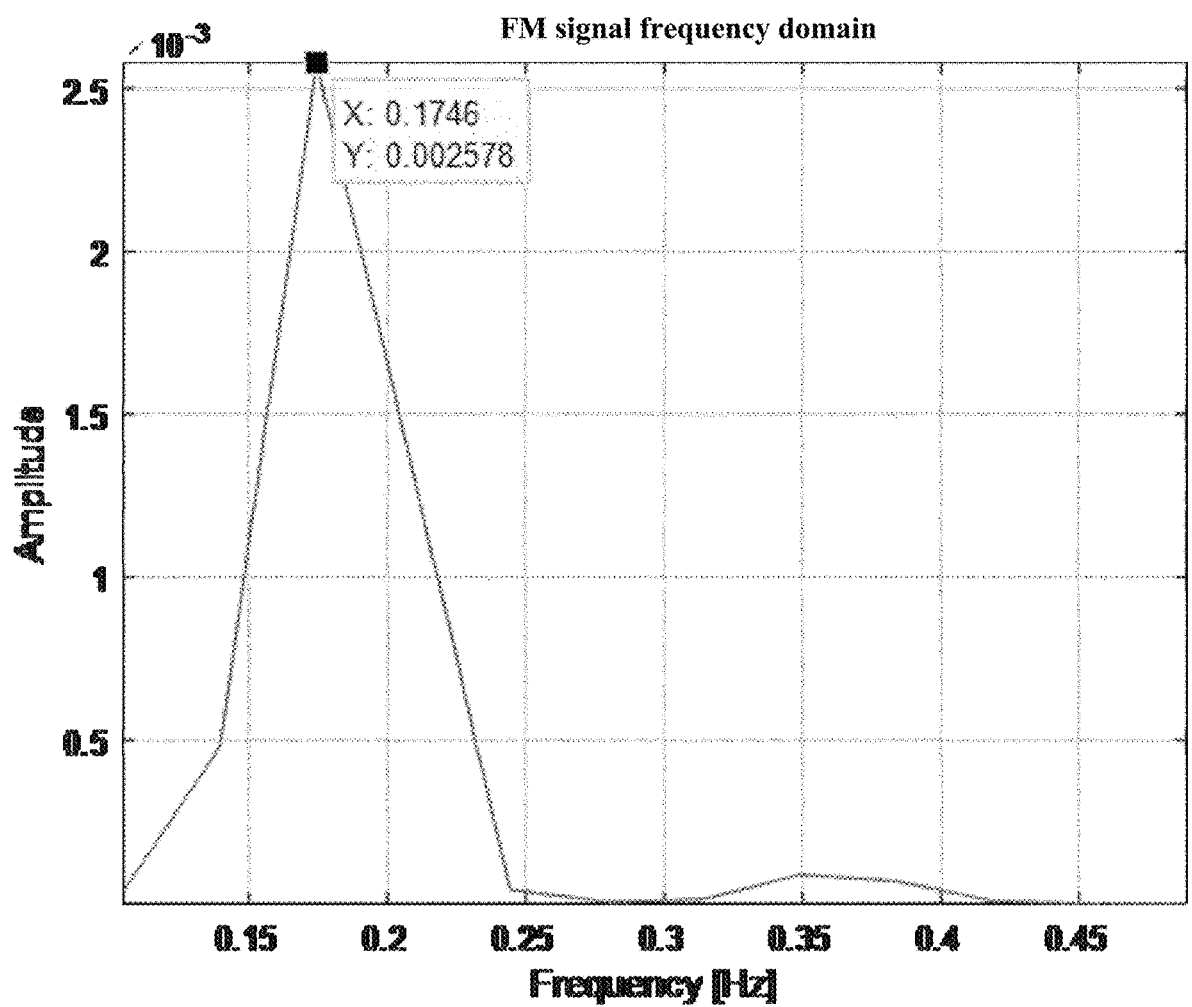
FIG. 18 shows a frequency-domain representation of the frequency modulation (FM) breathing signal from FIG. 16.

FIG. 18 shows a frequency-domain representation of the frequency modulation (FM) breathing signal from FIG. 16. The main harmonic can be seen as 0.1746 Hz, which is an FM signal calculated breathing rate of 10.48 breaths per minute.

Error Detection Methods Based on Comparing the AM Signal Vs the FM Signal:

In some embodiments, processor(s) can determine if the AM envelope main harmonics and FM between-pulse-time main harmonics are consistent with each other. To do so, the processor(s) can compare the AM envelope main harmonics with the FM between-pulse-time main harmonics, and check if these are close in value within a predetermined limit.

Here, for example, the invention can determine a respiration rate average based on both signals. That is, there is one respiration rate for the AM signal, and another for the FM signal. The agreement of these results provides confidence in the respiration rate average. A significant disagreement of these results indicates a potential error condition.

Based on experimental studies, we have found that the AM signal should be given a higher weight than the FM signal for optimal accuracy (versus a reference respiration rate). However, when the calculation of the respiration rate from the AM signal differs from that calculated from the FM signal by a specific ratio of the AM result, then the accuracy performance of the final result is likely to be lower than desired. This may be a possible error condition, or at least a caution indication. The processor can be configured to report warnings or errors depending on these results.

Based on experimental studies, we have further found that to improve confidence in the final breathing rate result, the processor should preferably make a comparison between the result coming from the AM signal against that coming from the FM signal. For example, this can be done by determining the respiratory rate average RRA, where:

$$|RRA_{AM} - RRA_{FM}| > r * RRA_{AM}.$$

In some embodiments, if this confidence check fails, then the processor is configured to return an error message rather than a breathing rate.

Further, in some embodiments, the final reported respiration rate may be determined to be a weighted combination of the AM result and the FM result.

For example, in some embodiments, the system may compute a weighted combination of the AM result and the FM result following the respiratory rate average (RRA) equation:

$$RRA = (a_1 * RRA_{AM}) + (a_2 * RRA_{FM}) + b.$$

Here, the weighting coefficients, $a_1$ and $a_2$, and offset, b, may be determined experimentally (e.g., through optimization of performance during algorithm calibration), and may then be stored in the device's memory for future use.

The invention claimed is:

1. A method of automatically determining a breathing rate of a patient, said method comprising:

obtaining pulse waveforms from an oscillometric device mounted on a limb of said patient, said pulse waveforms thus being oscillometric type pulse waveforms;

analyzing said pulse waveforms, using at least one processor, and determining artifact-free regions of said pulse waveforms, thus obtaining edited pulse waveforms;

analyzing said edited pulse waveforms, using said at least one processor, and determining AM envelope signals and FM between-pulse-time signals of said edited pulse waveforms;

analyzing said AM envelope signals and said FM between-pulse-time signals using said at least one processor, and determining an AM envelope main harmonic of said AM envelope signals and an FM between-pulse-time main harmonic of said FM between-pulse-time signals;

in response to said AM envelope main harmonic and said FM between-pulse-time main harmonic being within a predetermined limit of each other, using said at least one processor to calculate a value from a function comprising said AM envelope main harmonic and said FM between-pulse-time main harmonic;

and record or output said value as said breathing rate of said patient.

2. The method of claim 1, wherein said oscillometric device further comprises a tri-axial accelerometer-gyroscope device comprising a tri-axial accelerometer and/or a tri-axial gyroscope sensor, said tri-axial accelerometer-gyroscope device reports limb movement of said oscillometric device to said at least one processor, and said at least one processor further uses said limb movement to determine at least some of said artifact-free regions of said pulse waveforms.

3. The method of claim 2, wherein said at least some of said artifact-free regions of said pulse waveforms are determined by obtaining oscillometric cuff deflation signals, and analyzing said cuff deflation signals by any of:

a) analyzing areas where neighboring pulses exhibit below average cross-correlation;

b) obtaining any of tri-axial gyroscope signal or tri-axial accelerometer signals from said tri-axial accelerometer-gyroscope device and automatically deweighting those cuff deflation signals obtained during a time that said tri-axial accelerometer-gyroscope device detects motion above a preset threshold; and c) analyzing said AM envelope signals of said edited pulse waveforms, and automatically deweighting pulse waveform data associated with envelope outliers above a preset threshold.

4. The method of claim 1, wherein said at least one processor determines said AM envelope signals by determining an oscillometric envelope of pulse peak amplitudes, and determining a time varying amplitude of said AM envelope signals.

5. The method of claim 1, wherein said at least one processor further determines said FM between-pulse-time signals by computing time differences between peak indices of said pulse waveforms, and using these time differences to compute instantaneous pulse rates of said patient;

and wherein said at least one processor further uses said instantaneous pulse rates to determine said FM between-pulse-time signals.

6. The method of claim 1, wherein at least one processor determines said AM envelope main harmonic by determining a power spectral density of the main harmonics of an oscillometric envelope of said pulse waveforms; and wherein said at least one processor determines said FM between-pulse-time main harmonic by determining a power spectral density of an instantaneous pulse rate signal that is based on individual pulse positions of the pulse waveforms with respect to each other in time.

7. The method of claim 1, wherein said breathing rate is a weighted combination of said AM envelope main harmonic and said FM between-pulse-time main harmonic.

8. The method of claim 1, wherein said limb of said patient comprises a wrist of said patient, and said oscillometric device is mounted on said patient's wrist.

9. The method of claim 8, wherein said oscillometric device comprises said at least one processor, and said oscillometric device further comprises a display configured to display said breathing rate of said patient.

10. A system for automatically determining a breathing rate of a patient, said system comprising:

an oscillometric device configured to be mounted on a limb of said patient, said oscillometric device comprising at least one processor, memory, pressure cuff, and pressure cuff sensor, said device configured to obtain pulse waveforms, said pulse waveforms thus being oscillometric type pulse waveforms;

said at least one processor configured to analyze said pulse waveforms, and determine artifact-free regions of said pulse waveforms, thus obtaining edited pulse waveforms;

said at least one processor further configured to analyze said edited pulse waveforms, and determine AM envelope signals and FM between-pulse-time signals of said edited pulse waveforms;

said at least one processor further configured to analyze said AM envelope signals and said FM between-pulse-time signals, and determine an AM envelope main harmonic of said AM envelope signals and an FM between-pulse-time main harmonic of said FM between-pulse-time signals;

said at least one processor configured to determine when said AM envelope main harmonic and said FM between-pulse-time main harmonic are within a predetermined limit of each other, and when within the predetermined limit of each other, to calculate a value from a function comprising said AM envelope main harmonic and said FM between-pulse-time main harmonic, and to record or output said value as said breathing rate of said patient.

11. The system of claim 10, wherein said oscillometric device further comprises a tri-axial accelerometer-gyroscope device comprising a tri-axial accelerometer and/or a tri-axial gyroscope sensor, said tri-axial accelerometer gyroscope device further configured to report limb movement of said oscillometric device to said at least one processor, and said at least one processor further configured to use said limb movement to determine at least some of said artifact-free regions of said pulse waveforms.

12. The system of claim 11, wherein said at least one processor is configured to determine said at least some of said artifact-free regions of said pulse waveforms by obtaining oscillometric cuff deflation signals, and analyzing said cuff deflation signals by any of:

a) analyzing areas where neighboring pulses exhibit below average cross-correlation;

b) obtaining any of tri-axial gyroscope signal or tri-axial accelerometer signals from said tri-axial accelerometer-gyroscope device and automatically deweighting those cuff deflation signals obtained during a time that said tri-axial accelerometer-gyroscope device detects motion above a preset threshold; and c) analyzing said AM envelope signals of said edited pulse waveforms, and automatically deweighting pulse waveform data associated with envelope outliers above a preset threshold.

13. The system of claim 10, wherein said at least one processor is further configured to determine said AM envelope signals by determining an oscillometric envelope of pulse peak amplitudes, and determine a time varying amplitude of said AM envelope signals.

14. The system of claim 10, wherein said at least one processor is further configured to determine said FM between-pulse-time signals by computing time differences between peak indices of said pulse waveforms, and using these time differences to compute instantaneous pulse rates of said patient;

and wherein said at least one processor further uses said instantaneous pulse rates to determine said FM between-pulse-time signals.

15. The system of claim 10, wherein said at least one processor is configured to determine said AM envelope main harmonic by determine a power spectral density of the main harmonics of an oscillometric envelope of said pulse waveforms; and wherein said at least one processor is configured to determine said FM between-pulse-time main harmonic by determining a power spectral density of an instantaneous pulse rate signal that is based on individual pulse positions of the pulse waveforms with respect to each other in time.

16. The system of claim 10, wherein said breathing rate is a weighted combination of said AM envelope main harmonic and said FM between-pulse-time main harmonic.

17. The system of claim 10, wherein said limb of said patient comprises a wrist of said patient, and said oscillometric device comprises a combined chassis and cuff device configured to be mounted on said patient's wrist.

18. The system of claim 17, wherein said oscillometric device further comprises any of a display configured to display said breathing rate of said patient, or a wireless transceiver configured to output said breathing rate of said patient.

* * * * *